(12) United States Patent
Samelson et al.

(10) Patent No.: US 9,050,273 B2
(45) Date of Patent: Jun. 9, 2015

(54) ULTRA FINE DEAD SEA MINERAL COMPOUND AND METHOD OF MANUFACTURE

(75) Inventors: Morris Samelson, San Antonio, TX (US); Johnathan M. Scharff, San Antonio, TX (US)

(73) Assignee: Morris Samelson, San Antonio, TX (US)

( * ) Notice: Subject to any disclaimer, the term of this patent is extended or adjusted under 35 U.S.C. 154(b) by 0 days.

(21) Appl. No.: 13/102,191

(22) Filed: May 6, 2011

(65) Prior Publication Data

US 2011/0212184 A1   Sep. 1, 2011

Related U.S. Application Data

(60) Continuation of application No. 12/118,299, filed on May 9, 2008, now abandoned, which is a continuation of application No. 10/601,796, filed on Jun. 23, 2003, now abandoned, which is a division of application No. 09/931,453, filed on Aug. 16, 2001, now Pat. No. 6,607,151.

(51) Int. Cl.
| | |
|---|---|
| *A61K 8/96* | (2006.01) |
| *A61K 8/04* | (2006.01) |
| *A61K 33/00* | (2006.01) |
| *A61Q 19/10* | (2006.01) |
| *B02C 18/06* | (2006.01) |
| *B02C 23/16* | (2006.01) |

(52) U.S. Cl.
CPC ............... *A61K 8/965* (2013.01); *A61K 8/044* (2013.01); *A61K 33/00* (2013.01); *A61K 2800/28* (2013.01); *A61Q 19/10* (2013.01); *B02C 18/062* (2013.01); *B02C 2023/165* (2013.01)

(58) Field of Classification Search
None
See application file for complete search history.

(56) References Cited

U.S. PATENT DOCUMENTS

| | | |
|---|---|---|
| 3,656,896 A | 4/1972 | Kern et al. |
| 4,002,462 A | 1/1977 | Maddox |
| 4,324,743 A | 4/1982 | Feuer et al. |
| 4,943,432 A | 7/1990 | Biener |
| 5,607,062 A | 3/1997 | Poser et al. |
| 5,705,172 A | 1/1998 | Efron et al. |
| 5,716,928 A | 2/1998 | Benet et al. |
| 5,747,002 A | 5/1998 | Clark et al. |
| 5,863,004 A | 1/1999 | Broillet |
| 5,876,702 A * | 3/1999 | Gers-Barlag et al. ............ 424/59 |
| 5,886,145 A | 3/1999 | Guilloux et al. |
| 5,997,889 A | 12/1999 | Durr et al. |
| 6,168,809 B1 | 1/2001 | DeLacharriere |
| 6,280,746 B1 | 8/2001 | Arquette et al. |
| 6,287,581 B1 * | 9/2001 | Krzysik et al. ................. 424/402 |
| 6,299,891 B1 | 10/2001 | Leverett |
| 6,365,656 B1 | 4/2002 | Green et al. |
| 6,367,723 B1 | 4/2002 | Kircher et al. |
| 6,458,388 B1 | 10/2002 | Genis et al. |
| 6,607,151 B2 | 8/2003 | Samelson |
| 6,716,441 B1 | 4/2004 | Osborne et al. |

FOREIGN PATENT DOCUMENTS

| | | | | |
|---|---|---|---|---|
| EP | 0937453 A2 | 8/1999 | | |
| EP | 1074245 A2 | 2/2001 | | |
| GB | 2262525 | 12/1991 | | |
| KR | 149428 B1 | 10/1998 | | |
| WO | WO 92/21741 | * 12/1992 | ............... | C11D 1/70 |
| WO | EP 0 937 453 | * 1/1999 | ............... | A61K 7/48 |

OTHER PUBLICATIONS

USPTO contracted translation of KR1994036647 with original Korean Text attached to the end, Oct. 24, 2013, 28 pages total.*
Ma'or "Skin smoothing effects of Dead Sea minerals: comparative profilometric evaluation of skin surface" International Journal of Cosmetic Science 19, 105-110 (1997).*
Tolman and Munson, 1903. Olive oils and olive oil substitutes. Journal of the American Chemical Society, vol. 25(9):954-962.

* cited by examiner

Primary Examiner — Thane Underdahl

(57) ABSTRACT

An ultra fine mineral compound and method of processing native Dead Sea minerals into this ultra fine mineral compound that can be used to manufacture all natural Dead Sea mineral compositions particularly compositions for use in bath and body products is disclosed. Even with the extreme ionic character of the Dead Sea minerals, the Dead Sea mineral compositions prepared remain in suspension creating a viable cosmetic preparation that can maintain adequate shelf life and provide a more pleasant feel for the consumer.

10 Claims, 4 Drawing Sheets

ULTRA FINE DEAD SEA MINERAL COMPOUND AND METHOD OF MANUFACTURE

This is a continuation of U.S. patent application Ser. No. 12/118,299, and any amendments thereof, filed May 9, 2008 now abandoned, which is a continuation of U.S. patent application Ser. No. 10/601,796 and any amendments thereof, filed Jun. 23, 2003 now abandoned and published as U.S. Publication 2004/0076600, which is a divisional application claiming priority to U.S. patent application Ser. No. 09/931,453 filed Aug. 16, 2001 now U.S. Pat. No. 6,607,151, all of which are hereby incorporated by reference.

BACKGROUND OF THE INVENTION

1. Field of the Invention

Applicant's invention relates to an ultra fine mineral compound and a method of processing native Dead Sea minerals into this ultra fine mineral compound that can be used to manufacture all-natural Dead Sea mineral compositions particularly compositions for use in cosmetic preparations such as bath and body products.

2. Background Information

A cosmetic product is any substance or preparation intended for placing in contact with the various external parts of the human body or with the teeth or mucous membranes of the oral cavity with the intention of cleaning, perfuming, or protecting, to keep such parts in good condition, change their appearance or correct body odors. There are numerous product groups that fall within the category of cosmetic products or preparations, including but not limited to cosmetic emulsions, deodorants and antiperspirants, sunscreens, make-up preparations, hair preparations, bath products, soaps, exfoliating agents, and shaving preparations.

Cosmetic preparations are usually mixtures. A mixture is any matter consisting of two or more substances physically combined in some proportion by mass. In a mixture there is no chemical reaction. Two types of mixtures are heterogenous mixtures and homogenous mixtures. A heterogenous mixture is a mixture having ingredients of different states of matter. A suspension is a heterogenous mixture in which droplets or particles are suspended in a liquid. A colloidal dispersion is a specific type of suspension in which the particles or droplets of one substance are smaller than those in suspensions, but larger than those in solutions and that have one dimension in the range of 1 to 10 nm. A homogenous mixture is a mixture having ingredients of the same states of matter. Homogenous mixtures are usually solutions which are made up of a solute dissolved in a solvent. When the solute does not remain dissolved in the solvent the mixture is in turn referred to as a heterogenous mixture.

Many cosmetic preparations are suspensions and more particularly colloidal dispersions. In a colloidal dispersion there is a suspension of finely divided particles in a continuous medium in which the particles do not settle out of the substance rapidly and are not readily filtered. Where the particle is a liquid droplet and the medium is a liquid, the colloid is referred to as an emulsion. If however the particle is a solid and the medium is a liquid, the colloid is referred to as a sol or gel. A sol is a colloidal dispersion of a solid in a liquid in which the particles are so small that the dispersion appears transparent while a gel is a suspension that behaves as an elastic solid or semi-solid rather than liquid.

Colloidal systems undergo agglomeration, or gathering into a mass, leading to a distribution of droplet size for liquid colloids. Though wetting phenomena and nonwetting colloidal factors may play a role, the agglomeration process is induced by particulate collisions arising from diffusion, as in Brownian motion, velocity or shear gradients in a liquid dispersion medium, and gravitational settling.

Irreversible agglomeration can be quantified using various models for repulsive or attractive electrostatic, London-van der Waals, and steric forces which affect stabilization of aqueous and nonaqueous colloidal systems. A comprehensive model of colloidal stability, the DLVO (Derjagiun-Landau-Verwey-Overbeek) model has provided information regarding the roles of electrolytes, dielectric constant, and other physical quantities in colloidal systems. This theory considers the electrostatic interactions between two identically charged, suspended particles to be repulsive and to arise from the overlap of the electrical double layers associated with each particle.

For systems containing a soluble polymer or surfactant, molecular arrangement, thickness of the absorbed layer, temperature, and chain or segment solvation are additional critical parameters in determining the effectiveness of a dispersed agent in providing steric stabilization. If velocity or shear gradients are present, such as in mixing, and are sufficiently large, the frequency of collisions depends on the volume fraction of solids and the mean velocity gradient. Assuming that sedimentation is slow compared to the first two collision mechanisms, the overall agglomeration rate is $$-dN/dt = k_d N^2 + k_s N$$

where N is the particle number concentration, $k_d$ and $k_s$ are the respective rate constants corresponding to diffusion controlled and shear induced collision processes, and the minus sign denotes that the particle number concentration decreases with time.

Cosmetic emulsions, such as lotions and creams, are emulsions of water-based and oil-based phases. An emulsion is more particularly a two phase system consisting of two incompletely miscible liquids, the internal or discontinuous phase dispersed as finite globules in the other termed the continuous phase. Emulsions can be classified according which liquid is dispersed in the continuous phase. Oil in water (o/w) emulsions have oil as the dispersed phase in water as the continuous phase. In water in oil (w/o) emulsions, the water is dispersed in the oil as the continuous phase.

Products that produce emulsions, or emulsifiers, can be classified as ionic or nonionic according to their behavior. An ionic emulsifier is composed of an organic lipophilic group and a hydrophilic group. The hydrophilic-lipophilic balance is often used to characterize emulsifiers and related surfactant materials. The ionic types may be further divided into anionic and cationic, depending on the nature of the ion-active group. The lipophilic portion of the molecule is usually considered to be the surface active portion. Nonionic emulsifiers are completely covalent and show no apparent tendency to ionize. Emulsifiers, being surface active agents, lower surface and interfacial tensions and increase the tendency of their solution to spread.

Mixing of cosmetic preparations is an important operation particularly in the preparation of heterogeneous mixtures such as suspensions and colloids since the actual steps involved can dictate whether the particles or droplets remain suspended continuously throughout the medium for a reasonable period of time to maintain an adequate shelf life and viability of the preparation. This becomes increasingly difficult when the desire of the manufacturer is to produce cosmetic preparations that contain all natural ingredients. Natural ingredients refer to ingredients obtained from nature such as extracted directly from plants or animal products as opposed to being produced synthetically.

The present composition contains all natural ingredients. One of the natural ingredients incorporated into the composition of the present invention is Dead Sea minerals. Dead Sea minerals are not to be confused with sea salt or Afrosalt® which has a different chemical composition. Sea salt is the compound remaining when oceanic sea water is evaporated, and contains primarily sodium and chloride and in some cases trace amounts of copper, manganese, nickel, fluorine, tin and iodine. The trace minerals can vary based upon the source of the sea water. Afrosalt® is a compound of inorganic salts derived from seawater containing 45%±31 sodium, 53%±3 chlorides, 3.6% magnesium, <7% sulphates, <3% calcium, <2% bromides, 0.49%±0.04 potassium, <0.3% iodides. The Dead Sea is a unique body of water, unlike any other and has a singular chemical composition. For years it has been known that treatments administered at the Dead Sea can bring about significant remissions in diseases such as psoriasis, psoriatic arthritis, rheumatoid arthritis, and osteoarthritis. It is not known what the mode of action is of the Dead Sea minerals. It is however believed that specific ions from the minerals play a role mainly as co-factors in enzymatic regulation activities in the metabolism of healthy skin. There are indications that magnesium is a co-factor for phosphate transferring enzymes and participates in c-AMP c-GMP balancing regulation, potassium may enhance $CO_2$ transport, and calcium is thought to regulate cell membrane permeability. Zinc may play a role as a co-factor in cell proliferation enzymatic regulation.

Electrolytes can be absorbed into the skin from mineral rich preparations. The skin is a multilayered membrane with certain absorption characteristics which are subject to change. Corneum cell walls are involved in the semi-permeable membrane system and are responsible for the osmotic properties of the corneum. The penetration of the electrolytes through the stratum corneum occurs in between the horny cells.

There are models that demonstrate specific ionic absorption through the human skin barrier. Concentration is the key. When applying a cosmetic preparation, the relevant concentration is the concentration gradient between each specific dissolved ion both outside and inside the skin surface. During the absorption process, a partitioning of minerals occurs from the vehicle to the skin. The nature of the cosmetic preparation is significant in determining the kinetics of mineral skin penetration. Another important factor is the pH in the various microenvironments of the skin. Ions in varying valences and cations in combination with different anions penetrate to differing extents. There are major differences in the extent of skin penetration in different areas of the body.

The face is one of the highest absorbing areas. Exposed surface area, frequency of dermal application, skin type, skin age, temperature, and contact time should be considered. Factors involved in the percutaneous absorption of cosmetic preparations include use of other topical or systemic drugs, application parameters such as area, amount, frequency, massage; formulation such as concentration, nature of the vehicle, occlusivity, pH; formulation components such as solvents, surfactants, perfumes, dyes, inert ingredients, active ingredients, preservatives, impurities; skin damage such as abrasion, detergents, organic solvents, climatic factors; and physiological factors such as nature of the skin, anatomical site, individual factors and hydration. Assuming electrolytes can be absorbed into the skin, dermal application of mineral rich cosmetics can prove beneficial. The goal therefore has been to incorporate the beneficial properties of the Dead Sea into cosmetics.

Over the past few years cosmetics have been marketed that incorporate Dead Sea minerals, including body and face masks with highly viscous dispersions, lotions and creams with the minerals in very low concentrations, and one phase aqueous solutions with the minerals in very low concentrations. The composition of Dead Sea minerals is very unique. The concentration of the divalent cations magnesium and calcium is very high compared with the monovalent cations, mainly sodium and potassium. In addition, the ionic strength of a solution of these minerals is very high. These two factors have a tremendous negative effect on the formation and stability of dispersions and emulsions, and strictly limit their concentration to a few percent of the weight of conventional cosmetic formulations.

As mentioned previously, according to the DLVO theory stabilization of dispersions of emulsions can be described as the result of the combined attraction and repulsion forces between the particles or droplets that are dispersed in continuous phases. For example, oil in water emulsions can be stabilized by the absorption of ionic surfactants onto the oil droplet surface which may become positively or negatively charged. The electric surface potential will cause repulsion between the approaching droplets. If the repulsion forces overcome the attraction forces the emulsion will be stable. The electric surface potential is strongly dependent on electrolyte concentration and on the valence of the counter ion in the solution. Therefore, the electrical repulsion is significantly reduced in systems that contain high concentrations of electrolytes in general, and divalent counterions in particular. This results in difficulties in formulating a cosmetic emulsion that contains electrolytes from the Dead Sea that is rich in magnesium and calcium divalent cations at high concentrations, and will be stable for the minimum required shelf life for a cosmetic product. In addition, the high concentration of electrolytes may cause salting out and precipitation of various components of any cosmetic preparation. This may also affect the texture and the appearance of the product, its viscosity, hydrophilic-lipophilic balance, crystallization, etc.

The present invention provides for a chemical composition for application to the skin comprising a mixture of at least 50% processed ultra fine Dead Sea mineral particles in a continuous all natural carrier medium where in the Dead Sea mineral particles do not rapidly settle out of the carrier medium which promotes a more shelf stable product. This chemical composition takes advantage of the ionic properties of the Dead Sea minerals and contains minerals of such a fine granularity that exfoliation is not as harsh to the skin, particularly of persons suffering from severe skin disorders. In addition, the carrier medium of the present invention contains all natural ingredients and is non-comedogenic so consumers do not have to be concerned about clogged pores.

The problems of the prior art are overcome by the present invention by processing the Dead Sea minerals into an ultra fine mineral compound and mixing this ultra fine mineral compound with select natural ingredients using a unique swift heating, chilling and mixing technique to produce cosmetic preparations, such as body scrubs, rubs, muds, creams, lotions, and related preparations. These cosmetic preparations contain greater than 50% concentration of Dead Sea minerals but maintain stability and preferable shelf life with a pleasant feel for the consumer.

SUMMARY OF THE INVENTION

It is an object of the present invention to provide a novel method for processing native Dead Sea minerals into an ultra fine mineral compound.

Still another object of the present invention is to provide a novel ultra fine mineral compound.

It is another object of the present invention to provide a novel method for using manufactured ultra fine Dead Sea minerals to manufacture all natural Dead Sea mineral compositions.

Another object of the present invention is to provide novel Dead Sea mineral compositions.

Yet another object of the present invention is to provide novel Dead Sea mineral body scrubs, rubs, muds, creams, lotions, and related preparations.

It is still another object of the present invention to provide a novel Dead Sea mineral body scrub that remains in suspension to sustain shelf life.

It is an additional object of the present invention to provide a novel Dead Sea mineral body scrub that is made from all natural ingredients.

Still another object of the present invention is to provide a novel body scrub that has as its primary ingredient Dead Sea minerals.

It is yet another object of the present invention to provide novel Dead Sea mineral compositions that provide the optimal concentration of each specific ion in skin cells.

Still another object of the present invention is to provide novel Dead Sea mineral compositions that provide a pleasant feel for the consumer.

An additional object of the present invention is to provide novel Dead Sea mineral compositions that provide the optimal delivery vehicle for the various ionic compounds.

Another object of the present invention is to provide novel Dead Sea mineral compositions that are not irritating to the skin.

In satisfaction of these and related objectives, Applicant's present invention provides an ultra fine mineral compound and a method of processing native Dead Sea minerals into this ultra fine mineral compound that can be used to manufacture all natural Dead Sea mineral compositions particularly compositions for use in bath and body products.

DETAILED DESCRIPTION OF THE PREFERRED EMBODIMENT

Figure 1:
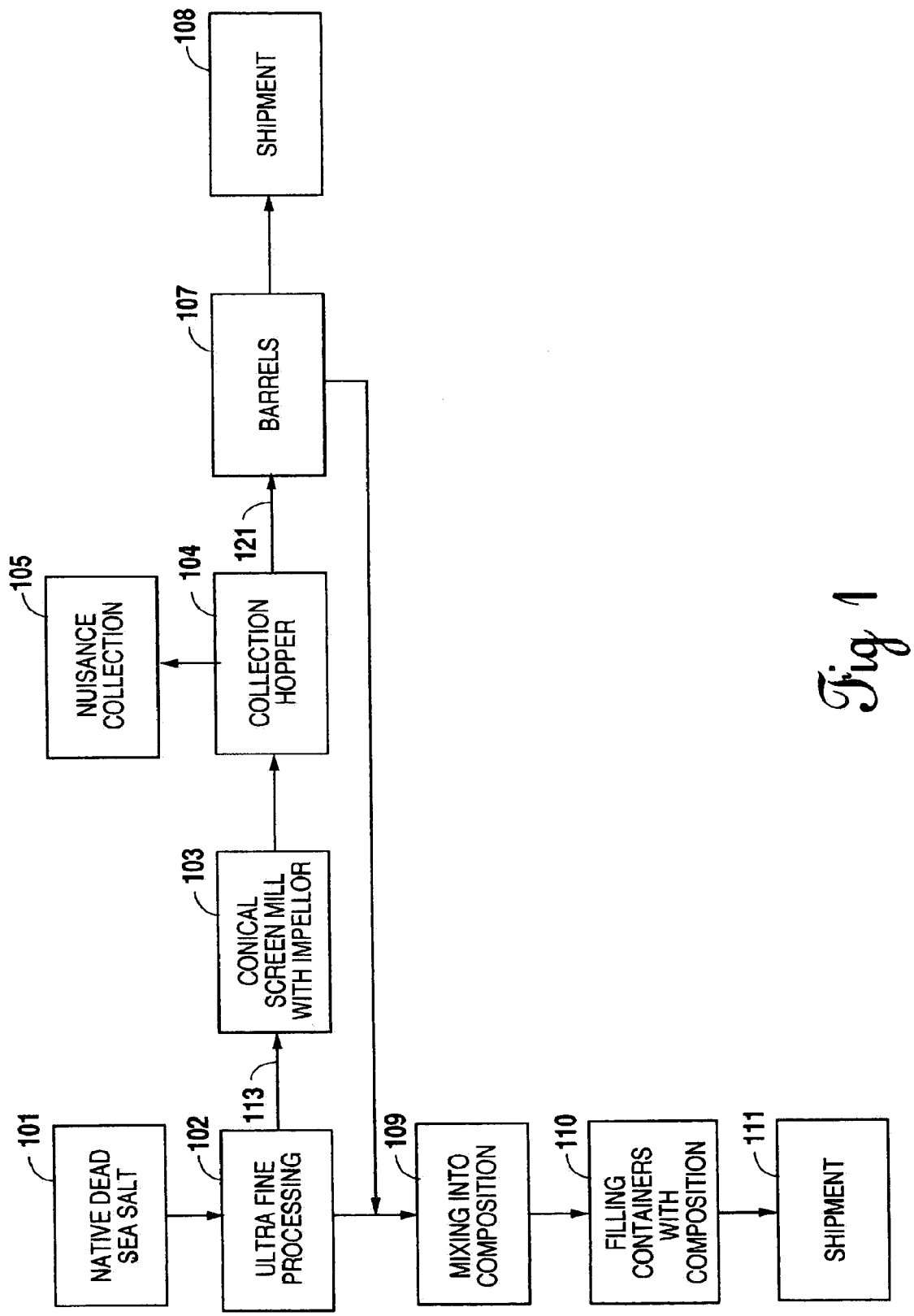
FIG. 1 is a flowchart of the organization of manufacture for the preferred embodiment of the present invention.
Figure 2:
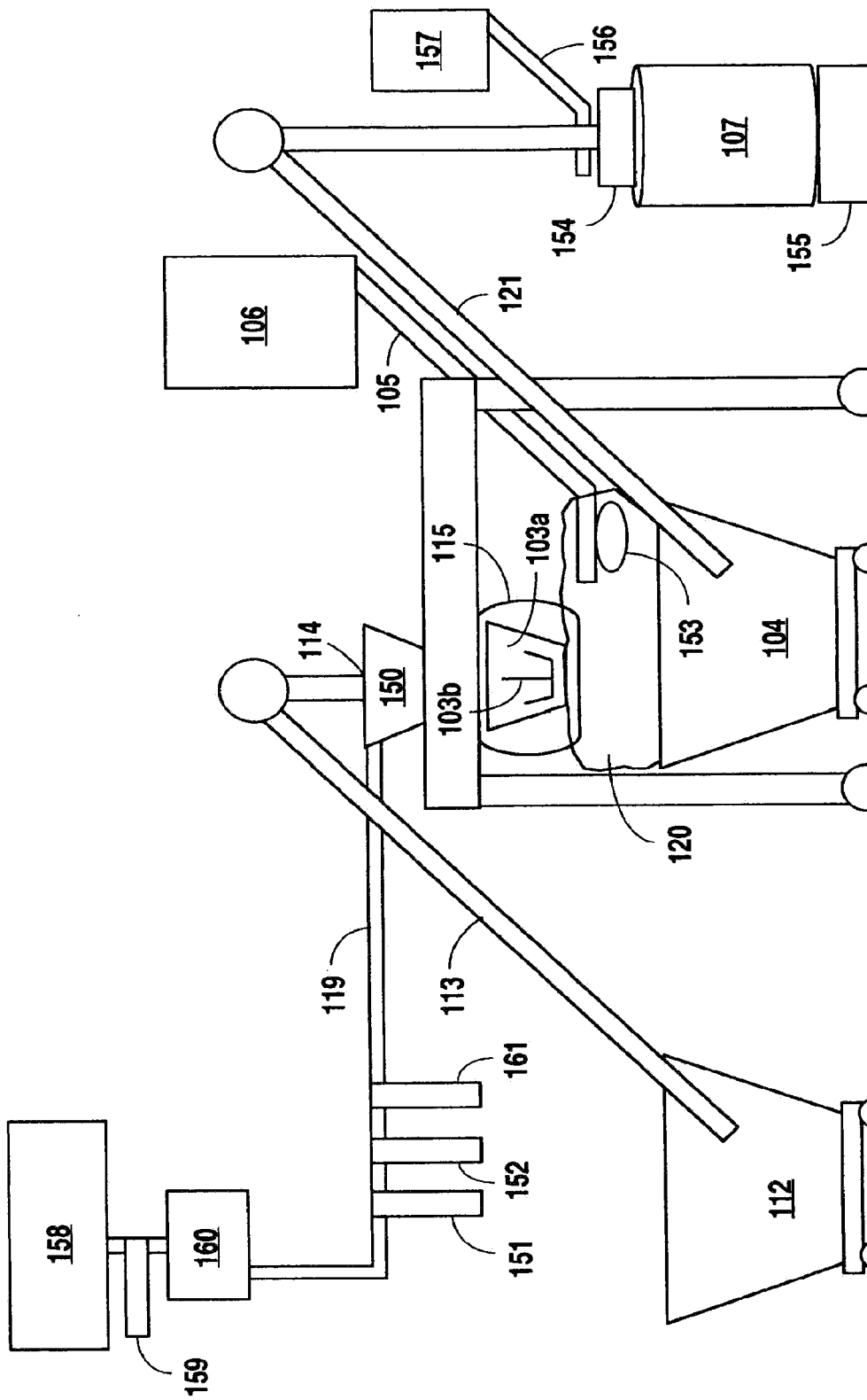
FIG. 2 is a perspective view of the conical screen mill system of the present invention manufacturing process.

Referring to FIG. 1, a flowchart of the organization of manufacture for the preferred embodiment of the present invention is shown. The Dead Sea mineral compositions and method for manufacture begins with the native Dead Sea minerals at step 101. The native Dead Sea minerals are typically composed of 31.0-35.0% magnesium chloride, 20.0-28.0% potassium chloride, 3.0-8.0% sodium chloride, 0.1-0.5% calcium chloride, 0.3-0.6% bromide, 0.05-0.2% sulfates, 0-0.3% insoluble minerals, and 32.0-40.0% water of crystallization. These values have a standard deviation of ±1%. These native Dead Sea minerals are next subjected to ultra fine processing at step 102. A perspective view of the conical screen mill and impeller system 103 is illustrated in more detail in FIG. 2. In the ultra fine processing, the native Dead Sea minerals are initially held in a hopper 112, that is preferably nonmetal, dispensed to a screw conveyor 113 and transported through a primary opening 114 into a second hopper 150. From second hopper 150, the native Dead Sea minerals are dispensed into a processor 115 that contains a conical screen mill with an impeller system 103 having preferably a dual headed impeller 103b. Once in the processor 115, the native Dead Sea minerals enter into the conical screen mill 103a. Within the conical screen mill 103a, the impeller 103b forces the native Dead Sea minerals through the conical screen 103a into a third hopper 104 thereby reducing the size of the native Dead Sea minerals and forming an ultra fine mineral compound. The conical screen mill with impeller system 103 not only reduces the particle size of the native Dead Sea minerals, but also keeps insoluble materials, such as pieces of hard mineral or rocks, from getting through so the ultra fine minerals that are formed are essentially "rock-free". The initial granularity of the native Dead Sea minerals is typically 31.3% not passing through US sieve 20 mesh, 40.2% not passing through US sieve 40 mesh, 24.6% not passing through US sieve 60 mesh, 2.5% not passing through US sieve 80 mesh, 0.4% not passing through US sieve 100 mesh, and 0.2% not passing through US sieve 120 mesh, 0.4% not passing through US sieve 200 mesh, and 0.3% pan. Simply, the preferred native minerals used in the present process have at a minimum 90% less than 10 mesh and 90% less than 1.7 mm size granularity. However, another grade of native minerals that can be used in the present process has a screen analysis that has at a minimum greater than 90% between 5 and 10 mesh and greater than 90% between 1.7 mm and 4.0 mm size granularity. In contrast, the granularity of the ultra fine minerals consist of typically 0.0% not passing through US sieve 20 mesh, 22.7% not passing through US sieve 40 mesh, 29.6% not passing through US sieve 60 mesh, 11.5% not passing through US sieve 80 mesh, 4.9% not passing through US sieve 100, 3.4% not passing through US sieve 120, 9.7% not passing through US sieve 200, and 18.2% pan.

A finer version of the minerals can also be obtained with a granularity of the minerals consisting of typically 0.0% not passing through US sieve 20 mesh, 0.4% not passing through US sieve 40 mesh, 16.0% not passing through US sieve 60 mesh, 15.0% not passing through US sieve 80 mesh, 8.7% not passing through US sieve 100 mesh, 5.5% not passing through US sieve 120 mesh, 16.2% not passing through US sieve 200 mesh, and 38.1% pan. The granularities for each of the minerals have a deviation of ±10%. The processing step for any version of the minerals ensures that 100% will have less than 10 mesh and 100% will have less than 1.0 mm size granularity.

At the primary opening of the processor 115, a specially fitted hose 119 is placed to regulate air into the impeller portion. This air originates from an attached air compressor 158. Before entering the impeller portion, the air passes through a pressure regulator 159 and through an air dryer 160. In addition, this air is filtered with preferably filters, one filter 151 that removes moisture and particulates and one carbon filter 152. By maintaining a cool, dry positive pressure environment the level of heat and moisture in the process remains low enabling the chemical composition to remain natural without the necessity of adding non-natural "free flowing" or "anti-caking" agents that would alter the natural composition. A secondary opening exists between the conical screen mill and impeller system 103 and third hopper 104 to allow for collection, but the remainder of this portion of processor 115 is kept closed with a cover 120, being preferably cotton or canvas, to prevent the ultra fine particulate from escaping into the air and causing possible respiratory problems and to prevent unnecessary moisture from entering the ultra fine minerals and altering their chemical coordination.

A nuisance collection tube 105, having a collection fitting, is placed adjacent opening 153 of third hopper 104 for super fine nuisance particulate debris collection into a nuisance collection receptacle 106. The processed ultra fine minerals are next conveyed along a screw type conveyor 121 to liner bags 154 within fibre drums or barrels 107 placed on a scale 155. A second nuisance collection tube 156 is placed from the screw type conveyor 121 for debris collection into a second nuisance collection receptacle 157. When 65 kg of ultra fine minerals are collected, the scale 155 automatically stops the screw type conveyor 121. All of the air is removed from the liner bag 154, the liner bag 154 is lock tied, and the barrel 107 closed. The barrel 107 is then transported to a pallet (not shown) for shipment 108. Both the native Dead Sea minerals and the ultra fine processed minerals are highly hygroscopic and therefore the entire process occurs in a modified room atmosphere with a temperature no higher than 78 degrees Fahrenheit with cool, dry positive pressure.

Figure 3:
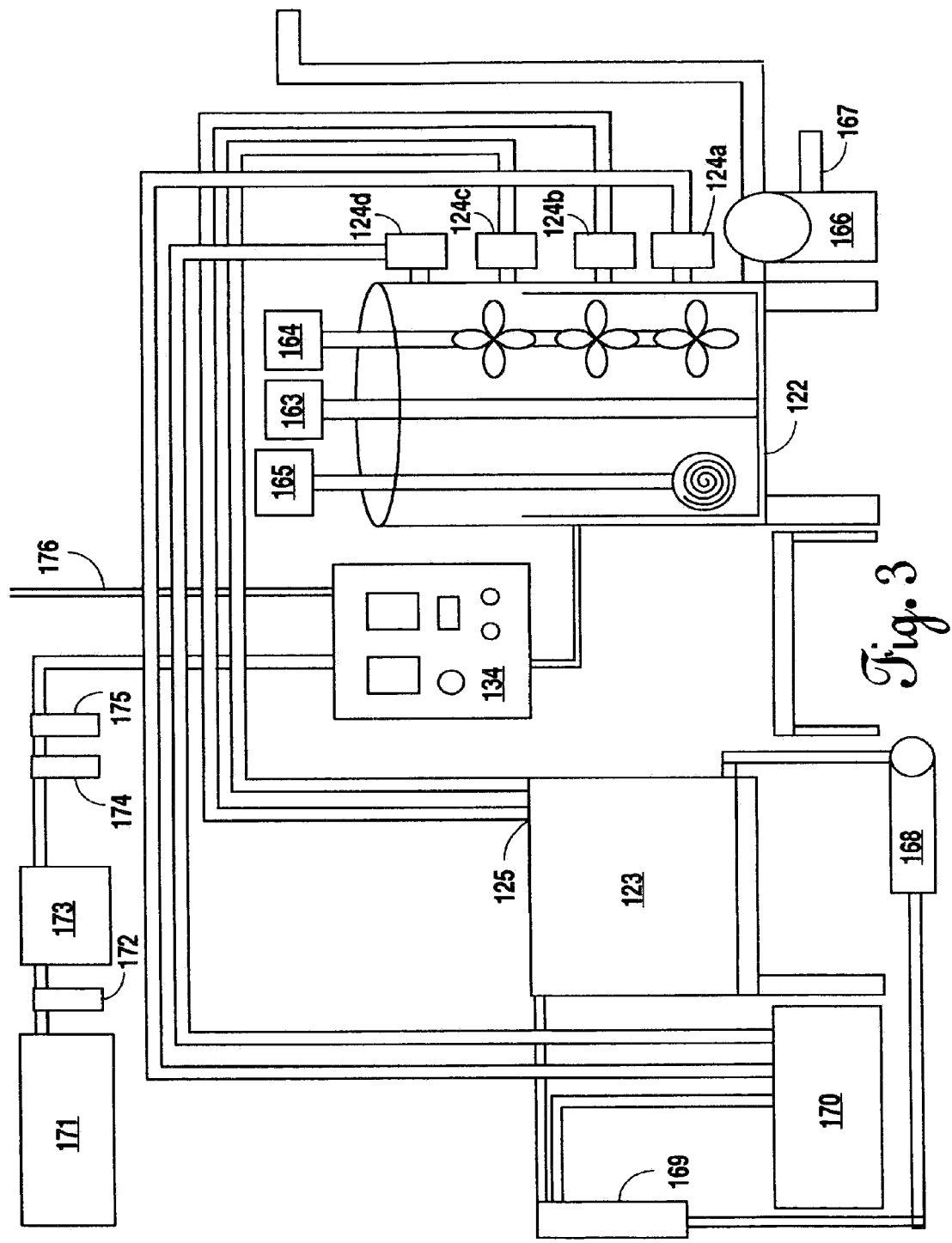
FIG. 3 is a perspective view of the unique swift heating, chilling and mixing system of the present invention.

Once the ultra fine minerals are prepared they can then be mixed at the mixing stage 109 into a Dead Sea mineral composition. The mixing step is illustrated in more detail with the perspective view of the swift heating, chilling and mixing system of FIG. 3. Swift heating or chilling for purposes of the present invention is defined as heating or chilling of a least about 200 gallons in about two hours or less. Mixing performance is evaluated primarily by the physical uniformity of the ultimate composition. The elements of the mixer design are the process design, such as the fluid mechanics of the impeller, fluid regimen required by the process, scale-up, and hydraulic similarity; impeller power characteristics, including speed and diameter; and mechanical design of the mixer, such as the impeller, shafts and drive assembly.

In preparing the Dead Sea mineral composition of the present invention it is important to consider the fluid mechanics of the mixing process. Mixer power, P, produces a pumping capacity Q expressed in kg/s, and a specific velocity work term of the head H expressed in J/kg according to the formula:

$$P=QH$$

where the term H is related to the square of the velocity and therefore to fluid shear rates. If the process is dependent primarily upon the pumping capacity, the fluid velocities and the individual shear rates, both on a macro- and a micro-scale are above a certain minimum level to allow other process requirements to proceed unhindered. If the pumping capacity is increased and some of the other velocity and shear rate values are decreased below some minimum, then fluid shear stress enters into the overall design.

When mixing the Dead Sea mineral composition of the present invention which involves at its simplest level a solid and at least one liquid, the settling velocity of the solid particles as well as the final viscosity of the suspension are critical factors in the process design as the ultimate goal is to obtain a composition that can be used as a cosmetic preparation with complete uniformity of the solid throughout the suspension that can be maintained not only through the mixing period, but also for a reasonable time thereafter for an adequate shelf life.

Figure 4:
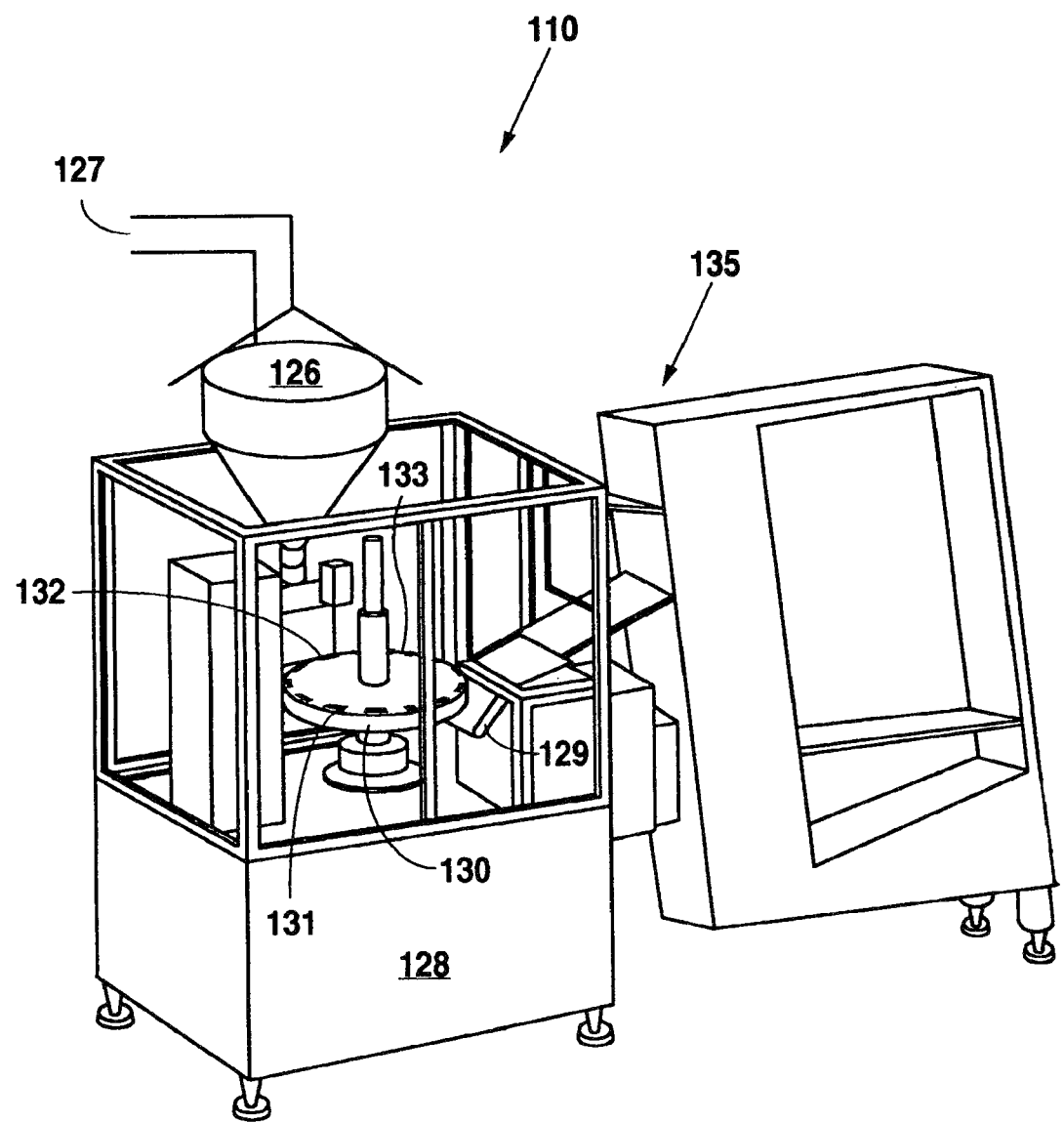
FIG. 4 is a perspective view of the tube packager of the present invention.

The process for preparing the Dead Sea mineral composition of the present invention utilizes water for many of its operations. The water originates from a local water source 168, then passes into a deionizer 169. The deionized water is then supplied to a boiler 170 and a chiller unit 123. Air is also incorporated into the system which originates from air compressor 171. The air passes from air compressor 171 through a pressure regulator 172 into an air dryer 173 to create cool dry air. The air then passes through a filter 174 and water trap 175 in process vessel 122. The process begins by heating the process vessel 122 and setting the temperature control on control panel 134 to 65 degrees Celsius to open the heat valves 124a and inject hot water from boiler 170 into the process vessel 122 jacket around the surrounding inside wall of the process vessel 122. Once circulated through process vessel 122 jacket, the water is returned out valve 124d. Liquid palm oil is added to vessel 122 once the vessel 122 begins to heat. When the temperature has reached at least 35 degrees Celsius, beeswax, jojoba wax PEG 120, cashew husk oil ethoxylate, and coconut oil are added to the process vessel 122 to begin melting. Scrape surface 163 agitation and triple impeller 164 agitation are turned on from control panel 134 at slow speed to mix (these are attached to a variable speed controlled motor). When these ingredients have reached 65 degrees Celsius and are melted thoroughly together then soybean oil, olive oil, jojoba oil, and vitamin E oils (Covitol 1250 and Covi-ox) are added. The speed of the scrape surface agitation and the triple impeller agitation are increased to medium. The heating is then turned off and the flow of hot water to the process vessel jacket 122 is closed. Turbine 165 agitation is then turned on within the process vessel 122 for high speed homogenous agitation or mixing. The ultra fine minerals are added and higher speed mixing with scrape surface 163 agitation and triple impeller 164 agitation is continued. The ultra fine minerals help to reduce the temperature. A chiller unit 123 is turned on and flow valves 125 are opened to circulate chilled water. The chiller unit 123 is itself chilled by an external cooling source such as a local water supply 168. The temperature control on the process vessel 122 is then set to 45 degrees Celsius to open the cooling valves 124b to the process vessel 122. The cold water is circulated through the process vessel 122 jacket and returned through valve 124c to chiller unit 123. Triple motion mixing is continued until the batch temperature reaches 45 degrees Celsius. Mixing of the batch with triple motion is continued at 45 degrees Celsius for another 15 minutes. The temperature control on control panel 134 is then set to 42 degrees Celsius and an essential oil blend is added (which is weighed and blended earlier) and mixing is continued. The batch is maintained at 42 degrees Celsius while mixing for 20-25 minutes. The temperature control on the process vessel 122 is then set to 40 degrees Celsius and mixing is continued. When the temperature of the batch reaches 40 degrees Celsius, package tubes can then be filled. At this stage, the batch is pumped from the process vessel 122 using pump 166 with a pressure regulator 167 to a holding hopper 126 at the filling station 128 of a tube packager 110. The tube packager 110 is illustrated in more detail in FIG. 4. As the level of the batch goes down in the holding hopper 126, the level sensor 176 signals the pump 166 to pump over more. The holding hopper 126 is covered except for the tube 127 that enters from the process vessel 122 due to the delicate nature of the batch product. Empty tubes are placed into a distribution station 135 and upon actuating the filling station 128 of the tube packager 110 the empty tubes are placed at station 129, oriented at station 130, filled at station 131, sealed at station 132, and trimmed into a final packaged Dead Sea mineral composition at station 133 ready for shipment 111. The tubes are preferably coextruded tubes with a barrier of protection between the mineral composition and the reactant tube surface.

The final Dead Sea mineral composition that can be used for cosmetic preparations such as body scrubs, rubs, muds, creams, lotions, and related preparations contains ultra fine Dead Sea minerals, palm oil, soybean oil, olive oil, jojoba oil, beeswax, essential oil blend, jojoba wax PEG 120, cashew husk oil ethoxylate, coconut oil, natural source Vitamin E oil (or d-alpha tocopherol), Vitamin E oil (or natural mixed tocopherols) used as antioxidant. The preferred essential oil blend includes rosewood, lavender, chamomile, and calendula.

Where the final composition is a body scrub, it contains preferably approximately 51% ultra fine Dead Sea minerals, 25% palm oil, 9.0% soybean oil, 5.0% olive oil, 3.0% jojoba oil, 3.0% beeswax, 1.0% essential oil blend, 1.0% jojoba wax PEG 120, 1.0% cashew husk oil ethoxylate, 1.0% coconut oil, 0.1% natural source Vitamin E oil or d alpha tocopherol, 0.05% Vitamin E oil or natural mixed tocopherols. The preferred essential oil blend for the body scrub includes 0.44% rosewood, 0.34% lavender, 0.20% chamomile, and 0.02% calendula. Even with the extreme ionic character of the Dead Sea minerals, the Dead Sea mineral compositions prepared remain in suspension creating a viable cosmetic preparation that can maintain adequate shelf life and provide a more pleasant feel for the consumer.

Conventional methods, known to those of ordinary skill in the art of cosmetics, can be used to administer the formulation of the present invention to a user; however, the preferred administration will be by transdermal delivery.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A composition for topical administration comprising, by weight, the following ingredients:
   a) about 50% or more of ultra fine Dead Sea minerals; and
   b) jojoba wax PEG 120 or cashew husk oil ethoxylate or a combination thereof;
      wherein the ultra fine Dead Sea minerals consist of particles,
      wherein 100% of the particles are less than 1.0 mm and the distribution of the particle sizes is less than or equal to ±10%,
      and wherein the composition does not comprise anti-caking agents or free flowing agents.

2. The composition of claim 1 further comprises an essential oil blend.

3. The composition of claim 2 wherein the essential oil blend comprises by weight:
   44% rosewood;
   34% lavender;
   20% chamomile; and
   2% calendula.

4. The composition of claim 1 wherein the amount of jojoba wax PEG 120 is about 1% by weight.

5. The composition of claim 1 wherein the amount of cashew husk oil ethoxylate is about 1% by weight.

6. The composition of claim 1 wherein the amount of jojoba wax PEG 120 is about 1% by weight and cashew husk oil ethoxylate is about 1% by weight.

7. The composition of claim 1, wherein the composition is a powder.

8. The composition of claim 1, wherein the composition is a suspension of the ultra fine dead sea salt minerals in ingredient b).

9. A chemical composition for application to the skin comprising:
   at least 50% by weight processed Dead Sea mineral particles,
      wherein the ultra fine Dead Sea minerals consist of particles,
      wherein 100% of the particles are less than 1.0 mm and the distribution of the particle sizes is less than or equal to ±10%,
      and wherein the composition does not comprise anti-caking agents or free flowing agents and
   a continuous carrier medium comprising:
      a) at least one essential oil; and
      b) jojoba wax PEG 120 or cashew husk oil ethoxylate or a combination thereof;
   wherein the particles are suspended uniformly in said carrier medium.

10. A powdered composition comprising, the following ingredients:
   a) Ultra fine Dead Sea minerals; and
   b) Jojoba wax PEG 120 or cashew husk oil ethoxylate or a combination thereof;
      wherein the ultra fine Dead Sea minerals consist of particles,
      wherein 100% of the particles are less than 1.0 mm and the distribution of the particle sizes is less than or equal to ±10%,
      and wherein the composition does not comprise anti-caking agents or free flowing agents.

* * * * *